US012412274B2

United States Patent
Qin et al.

(10) Patent No.: US 12,412,274 B2
(45) Date of Patent: Sep. 9, 2025

(54) METHOD AND SYSTEM FOR GENERATING GUIDE INFORMATION, AND COMPUTER-READABLE STORAGE MEDIUM

(71) Applicant: Infervision Medical Technology Co., Ltd., Beijing (CN)

(72) Inventors: Chunxia Qin, Beijing (CN); Shaokang Wang, Beijing (CN); Kuan Chen, Beijing (CN)

(73) Assignee: Infervision Medical Technology Co., Ltd., Beijing (CN)

( * ) Notice: Subject to any disclaimer, the term of this patent is extended or adjusted under 35 U.S.C. 154(b) by 398 days.

(21) Appl. No.: 18/072,923

(22) Filed: Dec. 1, 2022

(65) Prior Publication Data

US 2023/0177696 A1    Jun. 8, 2023

(30) Foreign Application Priority Data

Dec. 2, 2021    (CN) .......................... 202111473893.8

(51) Int. Cl.
*G06T 7/11*    (2017.01)
*G06T 7/00*    (2017.01)

(52) U.S. Cl.
CPC .............. *G06T 7/11* (2017.01); *G06T 7/0012* (2013.01); *G06T 2207/20081* (2013.01)

(58) Field of Classification Search
CPC ........................ A61B 10/0233; A61B 17/3403; A61B 34/10; A61B 34/20; A61B 2034/105;

(Continued)

(56) References Cited

U.S. PATENT DOCUMENTS 8,758,263 B1 *  6/2014  Rahimian .............. A61B 90/13
                                                        600/417
2007/0232882 A1 * 10/2007  Glossop ............. A61B 17/3211
                                                        600/407

(Continued)

FOREIGN PATENT DOCUMENTS

| CN | 109259806 A | 1/2019 |
| CN | 109549689 A | 4/2019 |

(Continued)

OTHER PUBLICATIONS

First Office Action issued in counterpart Chinese Patent Application No. 202111473893.8, dated May 10, 2022.

*Primary Examiner* — Katrina R Fujita
(74) *Attorney, Agent, or Firm* — Westbridge IP LLC (57) ABSTRACT

Disclosed are a method, a system, and an apparatus for generating guide information, and an electronic device. The method includes: obtaining image data to be identified of a detection target; segmenting the image data to be identified by using a trained image segmentation model to obtain segmented target image data; determining image data of positioning patches arranged on a body surface of the detection target in the target image data as feature points, and establishing a mapping relationship between a preoperative spatial three-dimensional image coordinate system and an intraoperative spatial positioning coordinate system; and generating guide information based on the mapping relationship, to guide a puncture needle to perform puncturing on the detection target. An operation time of a puncture operation can be greatly shortened, and puncture efficiency and accuracy can be improved.

16 Claims, 3 Drawing Sheets

(58) Field of Classification Search
CPC ...... A61B 2034/107; A61B 2034/2051; A61B 2034/2065; G06N 3/0442; G06N 3/0455; G06N 3/088; G06T 7/0012; G06T 7/11; G06T 7/33; G06T 2207/20081; G06T 2207/20084; G06T 2207/30064; G06T 2207/30204
See application file for complete search history.

(56) References Cited

U.S. PATENT DOCUMENTS

| | | | | |
|---|---|---|---|---|
| 2014/0018664 | A1* | 1/2014 | Weiss | A61B 5/72 600/414 |
| 2014/0276002 | A1* | 9/2014 | West | A61B 5/061 600/424 |
| 2015/0073259 | A1* | 3/2015 | Zhou | G01R 33/4812 600/407 |
| 2018/0303563 | A1* | 10/2018 | West | A61B 90/37 |
| 2019/0008591 | A1* | 1/2019 | Desai | G06T 7/0012 |
| 2019/0105109 | A1* | 4/2019 | Kato | A61B 6/032 |
| 2020/0155238 | A1* | 5/2020 | Tillett | A61B 17/3472 |
| 2021/0137634 | A1* | 5/2021 | Lang | A61B 90/98 |
| 2021/0236207 | A1* | 8/2021 | Stanton | A61B 34/30 |
| 2022/0000565 | A1* | 1/2022 | Gururaj | A61B 17/34 |
| 2022/0117674 | A1* | 4/2022 | Black | G06T 19/006 |
| 2022/0378526 | A1* | 12/2022 | Balicki | A61B 34/10 |
| 2023/0363832 | A1* | 11/2023 | Mosadegh | G16H 20/40 |

FOREIGN PATENT DOCUMENTS

| | | | |
|---|---|---|---|
| CN | 110464459 | A | 11/2019 |
| CN | 113100935 | A | 7/2021 |
| CN | 113610824 | A * | 11/2021 |
| CN | 113610826 | A | 11/2021 |
| WO | 2020100015 | A1 | 5/2020 |

* cited by examiner

METHOD AND SYSTEM FOR GENERATING GUIDE INFORMATION, AND COMPUTER-READABLE STORAGE MEDIUM

CROSS-REFERENCE TO RELATED APPLICATIONS

The present application claims priority to Chinese Patent Application No. 202111473893.8 filed on Dec. 2, 2021 and entitled "METHOD, SYSTEM, AND APPARATUS FOR GENERATING GUIDE INFORMATION, AND ELECTRONIC DEVICE", which is incorporated herein by reference in its entirety.

BACKGROUND

The present application relates to the field of image processing technologies, and in particular to a method and a system for generating guide information, and a computer-readable storage medium.

BACKGROUND

Nodules may refer to lumps or lesions with a solid shadow diameter less than 3 cm in imaging findings. The nodules may occur in any part of the body and are more common in parenchyma or on a surface of a parenchymal organ such as thyroid, breast, liver and gallbladder, lung, pancreas, and kidney. For example, pulmonary nodules are a multisystem and multiorgan granulomatous disease with unknown etiology, which often invades lungs, bilateral hilar lymph nodes, eyes, skin, and other organs, and its chest invasion rate is as high as 80% to 90%. The nodules are divided into solid nodules, partial solid nodules, and ground glass nodules. The partial solid nodules have the highest probability of malignancy, followed by the ground glass nodules and the solid nodules.

In order to be able to characterize a nodule at an early stage, pathological puncture is an inspection method to determine whether the nodule is benign or malignant, with relatively safe operation. At present, CT-guided percutaneous lung biopsy is an important method for clinical diagnosis of benign and malignant nodules, and this method has extraordinary diagnostic value in determining the nature of a nodule. CT-guided percutaneous puncture has become a basic, important, and indispensable medical skill in clinical work such as CT-guided percutaneous puncture and drainage, positioning, biopsy, radiofrequency ablation, particle implantation, and other medical diagnosis and treatment measures. A puncture doctor needs to master puncture skills proficiently, and accurately perform puncture for a target lesion. Accurate and safe CT-guided puncture can improve accurate diagnosis and treatment of a patient and reduce risks of the patient.

Therefore, there is an urgent need to provide a more reliable puncture guide solution.

SUMMARY

In view of this, embodiments of the present application aim to provide a method and a system for generating guide information and a computer-readable storage medium, which can overcome defects such as poor puncture operation accuracy, large radiation damage, and invisible target area in the prior art, thereby improving puncture efficiency and accuracy.

According to a first aspect of an embodiment of the present application, a method for generating guide information is provided, including:
   obtaining image data to be identified of a detection target;
   segmenting the image data to be identified by using a trained image segmentation model to obtain segmented target image data, where the target image data at least includes image data of positioning patches arranged on a body surface of the detection target;
   determining the image data of the positioning patches as feature points, and establishing a mapping relationship between a preoperative spatial three-dimensional image coordinate system and an intraoperative spatial positioning coordinate system; and
   generating guide information based on the mapping relationship, where the guide information is used to guide a puncture needle to perform puncturing on the detection target.

According to a second aspect of the present application, a system for generating guide information is provided, including:
   a puncture guiding device and positioning patches.

The puncture guiding device is communicatively connected to an image capturing device.

The positioning patches are communicatively connected to the puncture guiding device, and the puncture guiding device is configured to performing the following steps: receiving image data to be identified of a detection target, captured by the image capturing device; segmenting the image data to be identified by using a trained image segmentation model to obtain segmented target image data, wherein the target image data at least comprises image data of positioning patches arranged on a body surface of the detection target; determining the image data of the positioning patches as feature points, and establishing a mapping relationship between a preoperative spatial three-dimensional image coordinate system and an intraoperative spatial positioning coordinate system; and generating guide information based on the mapping relationship, wherein the guide information is used to guide a puncture needle to perform puncturing on the detection target.

According to a third aspect of an embodiment of the present application, a non-transitory computer-readable storage medium is provided. The non-transitory computer-readable storage medium stores computer program instructions, and the computer program instructions are run by a processor, the processor is configured to implement the method according to any one of the foregoing embodiments.

According to the method for generating guide information according to the embodiment of the present application, the image data to be identified of the detection target is obtained; the image data to be identified is segmented by using the trained image segmentation model to obtain the segmented target image data; the image data of the positioning patches arranged on the body surface of the detection target in the target image data is determined as feature points, and the mapping relationship between the preoperative spatial three-dimensional image coordinate system and the intraoperative spatial positioning coordinate system is established; and the guide information is generated based on the mapping relationship, to guide the puncture needle to perform puncturing on the detection target. Based on the foregoing method, a plurality of positioning patches are used to track a posture of the detection target, the image segmentation model is used to automatically detect and segment the image data to be identified, and the segmented image data of the positioning patches serves as feature points to implement efficient and rapid registration of DICOM image space and navigation positioning space. The generated guide information may provide intuitive feedback on a relative position between an anatomical structure of the detection target and the puncture needle as well as between the puncture needle and a planned path, greatly shortening an operation time and improving puncture efficiency and accuracy.

BRIEF DESCRIPTION OF THE DRAWINGS

Through a more detailed description of the embodiments of the present application with reference to the accompanying drawings, the above and other purposes, features and advantages of the present application will become more obvious. The accompanying drawings are provided for further understanding of the present application, and constitute a part of the present application. The accompanying drawings and the embodiments of the present application are used to explain the present application and do not constitute a limitation to the present application. In the accompanying drawings, a same reference symbol is used for representing a same component or step.

DETAILED DESCRIPTION OF THE EMBODIMENTS

The technical solutions of embodiments of the present disclosure will be described clearly and completely as below with reference to the accompanying drawings of the embodiments of the present disclosure. Apparently, the described embodiments are merely part of the embodiments of the present application, but not all of them. All other embodiments obtained by a person of ordinary skill in the art based on the embodiments of the present disclosure without paying any creative effort shall fall into the protection scope of the present disclosure.

Overview

CT-guided percutaneous lung biopsy is a technique for performing percutaneous lung biopsy with accurate positioning under CT guide. CT-guided percutaneous puncture currently has become an important means of diagnosis and identification of nodules or lumps. Especially the CT-guided percutaneous puncture is particularly valuable for lesions located in a peripheral area of lung that cannot be reached. Percutaneous puncture is a minimally invasive surgery with less damage, which mainly uses a fine needle to extract a sample or inject a drug through local skin and a local tissue or organ, so as to achieve purpose of diagnosis and treatment. Puncture surgery is of great value for diagnosis of infectious diseases, hemorrhagic diseases, tumors and other diseases, and may also be used for treatments such as preoperative anesthesia, serous cavity gas and fluid removal, and intrathecal injection. Moreover, due to small trauma and quick recovery, the puncture surgery is widely used in clinical practice.

Computed Tomography (CT) of chest or abdomen is a method of examining the chest or abdomen with X-ray computed tomography. The CT of chest is used as an example. Generally, there are many layers for the CT of chest, and images displayed at each layer are different. If there is no abnormality, a doctor is written in the report as follows: The plain scan of the lung window shows that the texture of both lungs is clear, the direction and distribution of both lungs are normal, and there is no exudation or space-occupying lesions in the lung parenchyma. The mediastinal window shows that the two pulmonary hila are not enlarged, trachea and bronchus are unobstructed, the enhanced blood vessels and fat spaces are clear, and there is no enlarged lymph node in the mediastinum. No abnormalities are found in pleura, ribs and soft tissue of chest wall. Impression: No abnormalities are found in chest CT scan. In the early stage of viral pneumonia: generally only the lung markings are increased and blurred. Lesion progression: Reticular and small nodular shadows are diffused in both lungs. For severe cases, there are patchy or large patchy shadows, which are single or multiple, or diffusely distributed in both lungs. The shadows are mostly ground-glass density nodules, and may also progress to alveolar consolidation images. Diffuse emphysema occurs in both lungs due to inflammatory stenosis of the bronchiole.

For example, in the existing pulmonary nodule puncture solution, free-hand marked puncture or laser-assisted puncture is used. A general process of the free-hand marked puncture plan is as follows: A patient is in prone position, palpation is performed and iliac crest and lumbar spinous process of the patient are marked with lines by using a marker, and the highest points of the iliac crest are found and connected with a line as a reference for the needle insertion point. The bony landmark on the body surface is used as a reference to estimate a target puncture gap. A grid-shaped localizer is placed on the body surface, and a position of the target gap in the localizer is observed and marked with a C-arm X-ray machine. An intersection of the target gap and a lateral edge of the intervertebral foramen is a projection point of a target point on the body surface. The needle insertion point is 10-14 cm away from the midline of the spinous process, which is specifically depending on individual differences and different gaps. A connection line between the projection point of the target point on the body surface and the needle insertion point is a body surface projection of a puncture route.

A general process of the laser-assisted puncture is as follows: A bracket is an inverted L-shaped aluminum alloy structure, and the bottom is a tripod support, connected to a vertical rod. A height of the bracket is adjustable (1.2-1.7 m), and may be locked with a wrench. The bracket may alternatively be disassembled for easy portability. There are a drum-type angle plate (0°-360°), an adjustable angle plate (0°-40°), and a laser light source at the end of a horizontal rod. A laser light source switch and a charging socket are located on the side of the drum-type angle plate. A roller on the back side may adjust an angle of the laser light source, and there is a scale line in the center of the light source, which serves as a reference line for angle adjustment.

The current related technologies mainly rely on external equipment to mark a physical space, and confirmation of a marking position still requires a large number of manual verification links. The nodule target cannot be seen directly, and repeated confirmation is required during a puncture process to ensure accurate palpation of a nodule. Therefore, there is a need to improve puncture accuracy and efficiency.

To resolve the foregoing technical defects, an embodiment of this specification provides a guide information generation solution, which is used in combination with a specific electromagnetic tool. In the solution, an artificial intelligence technology is used to analyze chest and abdominal CT images, automatically perform three-dimensional image reconstruction, and assist a practitioner in analyzing a spatial relationship between a target lesion and an important anatomical structure and performing preoperative planning of a surgical procedure for navigation of a puncture procedure of solid organs such as an adult lung and abdomen.

Next, the embodiments provided in this specification are described.

Exemplary Methods

A method for generating guide information according to an embodiment of this specification is described below in detail with reference to the accompanying drawings.

Figure 1:
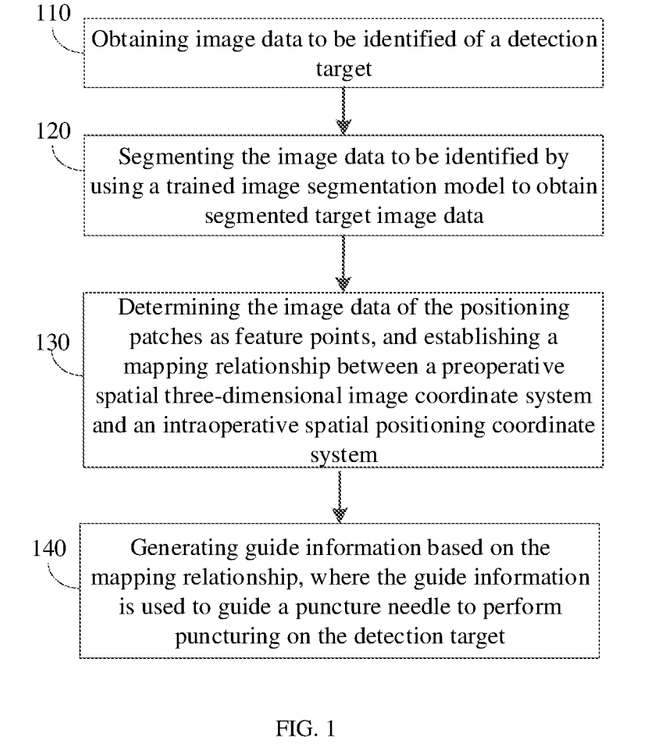
FIG. 1 is a schematic flowchart of a method for generating guide information according to an embodiment of this specification.

FIG. 1 is a schematic flowchart of the method for generating guide information according to the embodiment of this specification. From a program perspective, a process may be performed by a program mounted on an application server or an application client. In this embodiment, the process may be performed by a server cluster in a guide information generating device, and the server cluster may receive scanned patent image data of a patient and process the image data of the patent, and may further generate guide information for puncture guide.

As shown in FIG. 1, the process may include the following steps.

Step 110: Obtaining image data to be identified of a detection target.

The detection target may represent a patient to be detected in the embodiment of this specification. In an actual application scenario, a hospital may be equipped with a guide information generating device. The patient to be detected lies on a magnetic field generator according to a position (a supine position, a lateral position, or a prone position) required by a doctor. Positioning patches are fixed on a body surface of the patient for monitoring.

The image data to be identified may be image data, collected by an image capturing device, of the patient to be detected. For example, the image data to be identified may be CT image data, collected before puncture by the image capturing device, of the patient to be detected. The image capturing device may represent a medical image capturing device in the embodiment of this specification.

Step 120: Segmenting the image data to be identified by using a trained image segmentation model to obtain segmented target image data, where the target image data at least includes image data of positioning patches arranged on a body surface of the detection target.

The trained image segmentation model may be a trained deep learning model, and the deep learning model is used to perform image segmentation on the image data to be identified. For the image segmentation model, in an identification process, an input data source may be image data, collected by the medical image capturing device, of the patient to be detected, and an output result may be segmented image data. In a training process, a source of training sample data may be complete patient medical image data in a hospital information system, and the hospital information system may include medical image data of all patients.

It should be noted that, the image segmentation model in the embodiment of this specification can learn features of different organ types, different lesion area types, and different positioning patch types in the training process. In the identification process, the image segmentation model may extract organ features, lesion area features, and positioning patch features in the image data to be identified, and identify different organs, lesion areas, non-lesion areas, and the positioning patches with different features based on these features in the identification process, so as to perform segmentation.

The positioning patches may be used for auxiliary fixation of the patient's body position, so that positioning and repositioning in a monitoring process are accurate, and fixation is firm, thereby improving a treatment effect and reducing damage to a normal human tissue.

Step 130: Determining the image data of the positioning patches as feature points, and establishing a mapping relationship between a preoperative spatial three-dimensional image coordinate system and an intraoperative spatial positioning coordinate system.

In an actual detection process, the positioning patches are attached to the body surface of the patient. During preoperative image collection, image information of the body surface of the patient includes information about the positioning patches. During an operation, a puncture navigation image also includes the image data of the positioning patches. Based on the preoperative spatial three-dimensional image coordinate system and the intraoperative spatial positioning coordinate system of the positioning patches, the mapping relationship between preoperative image data and intraoperative spatial positioning data of the detection target may be established.

Step 140: Generating guide information based on the mapping relationship, where the guide information is used to guide a puncture needle to perform puncturing on the detection target.

The guide information may be information used to guide the puncture needle to perform puncturing on the detection target. Specifically, the guide information may be one or more of image information, text information, and voice information. The guide information may at least include a puncture path, and the puncture path may include the needle insertion point, a needle insertion direction, a needle insertion distance, and the like.

According to the method in FIG. 1, the image data to be identified of the detection target is obtained; the image data to be identified is segmented by using the trained image segmentation model to obtain the segmented target image data; the image data of the positioning patches arranged on the body surface of the detection target in the target image data is determined as feature points, and the mapping relationship between the preoperative spatial three-dimensional image coordinate system and the intraoperative spatial positioning coordinate system is established; and the guide information is generated based on the mapping relationship, to guide the puncture needle to perform puncturing on the detection target. Based on the foregoing method, a plurality of positioning patches are used to track a posture of the detection target, the image segmentation model is used to automatically detect and segment the image data to be identified, and the segmented image data of the positioning patches serves as feature points to implement efficient and rapid registration of DICOM image space and navigation positioning space. The generated guide information may provide intuitive feedback on a relative position between an anatomical structure of the detection target and the puncture needle as well as between the puncture needle and a planned path, greatly shortening an operation time and improving puncture efficiency and accuracy.

Based on the method illustrated in FIG. 1, an embodiment of this specification further provides some specific implementations of the method, which are described below.

The positioning patches used in the embodiments of this specification have different features, and specifically, the positioning patches may have different shapes or different sizes, or have different transmit signal strengths. For example, three positioning patches A, B, and C are used, where the patch A is cylindrical, the patch B is cubic, and the patch C is prismatic.

A signal transmitter or sensor may further be installed in the positioning patch, and the transmit signal strength may vary so as to represent different features of the positioning patches.

In the prior art, a position of an organ or a position of a positioning patch in a patient image generally needs to be manually marked, and the guide information is generated based on a positional correspondence between a preoperative image and an intraoperative image. However, due to a large workload of manual marking, marking accuracy is low, resulting in insufficient puncture efficiency and accuracy. On such a basis, in the embodiment of this specification, the positioning patches with different features are used as feature points to establish the mapping relationship between the preoperative image data and postoperative image data, which may be implemented in the following ways:

obtaining the preoperative image data of the positioning patches and intraoperative spatial positioning data of the positioning patches;
    obtaining first position information of each positioning patch in the preoperative image data;
    obtaining second position information of each positioning patch in the intraoperative spatial positioning data; and
    establishing the mapping relationship between the preoperative spatial three-dimensional image coordinate system and the intraoperative spatial positioning coordinate system based on the first position information and the second position information.

In a practical application scenario, position information of the positioning patch on the patient's body surface may be converted to be in a spatial coordinate system of intraoperative spatial positioning data during an operation. Therefore, the second position information of the positioning patch in the intraoperative spatial positioning data may represent information of an actual position where the positioning patch is arranged in the patient's body surface. The first position information of the positioning patch in the preoperative image data may represent coordinate system position information of the positioning patch in a spatial three-dimensional image. Based on the first position information and the second position information of the positioning patch, the mapping relationship between the preoperative spatial three-dimensional image coordinate system and the intraoperative spatial positioning coordinate system may be established.

The positioning patch may be provided with a sensor, and the sensor in each positioning patch may transmit position information of the corresponding positioning patch to a server cluster. After receiving preoperative image data to be identified, the server cluster may determine position information of each positioning patch in the preoperative image data to be identified in combination with the position information of each positioning patch, and the position information may be determined as the first position information.

Certainly, in practical applications, the position information of each positioning patch may alternatively be obtained in another manner, which is not specifically limited in the embodiment of this specification.

Compared with manually marking an organ as a feature point, the technical solution in the embodiment of this specification can improve efficiency of establishing the mapping relationship between the preoperative spatial three-dimensional image coordinate system and the intraoperative spatial positioning coordinate system. For a solution in which a same positioning patch is manually marked, the technical solution of using the positioning patches with different features as feature points in the embodiment of this specification can improve efficiency and accuracy of establishing the mapping relationship, further improving puncturing efficiency and accuracy.

After the mapping relationship is established, the guide information may be generated based on the mapping relationship, which may specifically include:

determining, based on the mapping relationship and according to a preset puncture rule, a puncture path for performing puncturing on the detection target, where the puncture path at least includes a needle insertion point, a needle insertion direction, and a needle insertion distance.

In a medical scenario, setting of the puncture path should follow a puncture rule. In the embodiment of this specification, the puncture rule may ensure that the puncture path avoids ribs and important organs. The puncture rule may include the following:

a) the puncture path should be as short as possible to avoid bleeding;
    b) the puncture path should avoid important anatomical structures such as ribs, blood vessels, and trachea;
    c) the puncture path should avoid the intercostal blood vessels, and try to insert the needle along the upper edge of the lower rib;
    d) the puncture path should avoid interlobar fissures to reduce the risk of pneumothorax; and
    e) the puncture path should avoid obvious infectious lesions.

Based on the foregoing puncture rule, the puncture path is set. The puncture path may represent a path taken by the puncture needle when puncturing is performed on a patient. During the puncture process, the puncture needle completes puncture according to the puncture path.

When a puncture operation is performed, in order to ensure puncture precision, a position of the puncture needle in the operation needs to be positioned based on a mapping relationship of the positioning patch, thus guiding the puncture needle in the operation for puncture.

Furthermore, the generation of the guide information may be implemented by using the following steps:

obtaining third position information of the puncture needle in the preoperative image data;
    determining, based on the first position information and the third position information, relative position information of the puncture needle and the positioning patch; and generating the guide information based on the relative position information and the mapping relationship.

The positioning patch is generally arranged near a part needing to be punctured for positioning and puncture. Therefore, the guide information may be generated based on the relative position relation between the puncture needle and the positioning patch, to guide the puncture needle to perform puncturing.

In the foregoing steps, the generation of the guide information may be implemented by using the following steps:

determining any one of the positioning patches in the preoperative image data as a reference positioning patch;

obtaining position coordinates of the reference positioning patch;

calculating, by using the position coordinates of the reference positioning patch as a reference, a first position correspondence between another positioning patch in the preoperative image data and the reference positioning patch;

calculating a second position correspondence between the reference positioning patch in the preoperative image data and the reference positioning patch in the intraoperative spatial positioning data;

calculating, based on the first position correspondence and the second position correspondence, position information of an intraoperative puncture needle in the intraoperative spatial positioning data; and generating the guide information based on the mapping relationship and the position information of the intraoperative puncture needle in the intraoperative spatial positioning data.

During determining of an intraoperative real-time position of the puncture needle, the foregoing method steps may be described with reference to FIG. 2.

Figure 2:
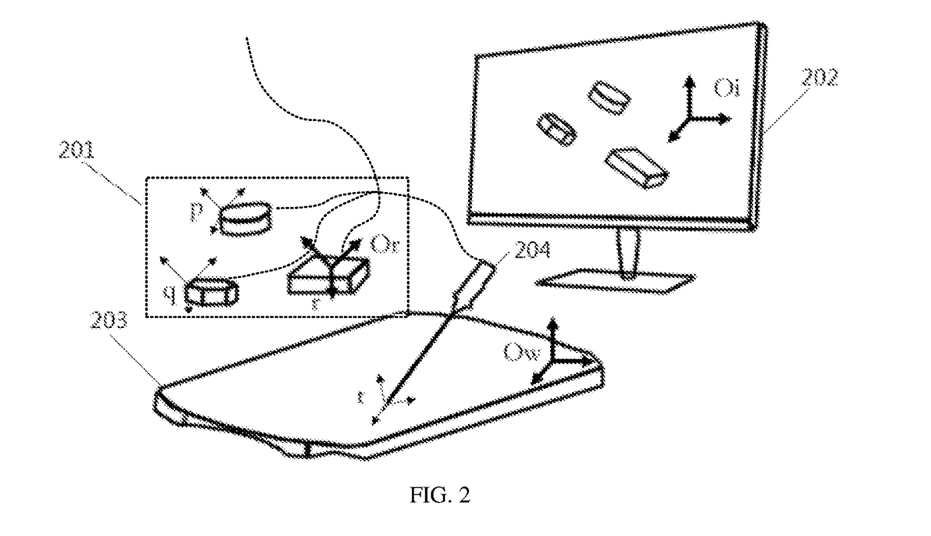
FIG. 2 is a schematic diagram of determining a real-time position of a puncture needle in a method for generating guide information according to an embodiment of this specification.

FIG. 2 is a schematic diagram of determining a real-time position of a puncture needle in a method for generating guide information according to an embodiment of this specification. As shown in FIG. 2, there are a plurality of positioning patches 201, a computer 202, a CT bed 203, and a puncture needle 204. The positioning patches 201 are used to track a posture of a patient during an operation. As shown in FIG. 2, the patient may lie on the CT bed 203, and the positioning patches 201 with different features may be arranged on the patient's body surface, to implement identification and positioning of each positioning patch 201 in image data. Each positioning patch 201 is in a one-to-one correspondence with an interface of a navigation tracker control unit. As shown in FIG. 2, the puncture needle 204 is provided with a sensor adapter buckle at a position of the needle end for connecting a positioning sensor. The positioning patches 201 and image information of the puncture needle 204 may be displayed on the screen of the computer 202.

During determining of the intraoperative real-time position of the puncture needle, it is assumed that the positioning patches 201 include three positioning patches p, q, and r. The positioning patch r is selected as a reference positioning patch Or, and position coordinates of the reference positioning patch Or are used as a benchmark to calculate a first position correspondence of each of the other positioning patches p and q relative to the reference positioning patch Or in the preoperative image data. The calculation in this step may be performed according to the following formula (1):

$$S_i^{Ref} = (M_{Ref}^{Tracker})^{-1} S_i^{Tracker} \quad (1)$$

The formula (1) represents a relative position of each positioning patch in a reference coordinate system. When an electromagnetic navigator starts to work, a space coordinate system generated by a magnetic field generator is defined as $O^{Tracker}$. $M_i^{Tracker}$ (i=1,2 ... n) indicates a posture of each positioning patch in $O^{Tracker}$; $M_p^{Tracker}$ indicates a spatial posture of the puncture needle in $O^{Tracker}$; The reference positioning patch is denoted as Ref, and the reference coordinate system is $O^{Ref}$; and $S_i^{Tracker}$ is a translation component of $M_i^{Tracker}$.

Then, a second position correspondence between the reference positioning patch Or and the reference positioning patch Oi may be calculated according to the following formula (2):

$$S_p^{LPS} = M_{Ref}^{LPS}(M_{Ref}^{Tracker})^{-1} S_p^{Tracker} \quad (2)$$

The formula (2) represents a real-time position of the puncture needle in a patient image coordinate system $O^{LPS}$. $S_i^{LPS}$ (i=1,2 ... n) indicates a coordinate position of each positioning patch in a DICOM image LPS coordinate system $O^{LPS}$ before puncturing is performed, where n denotes a quantity of positioning patches; $S_p^{Tracker}$ denotes a translation component of $M_p^{Tracker}$; $M_{Ref}^{LPS}$ denotes a transformation matrix from $O^{Ref}$ to the coordinate system $O^{LPS}$, and is obtained through calculation of rigid registration of coordinate sets $S_i^{Ref}$ and $S_i^{LPS}$ (i=1,2 ... n).

Certainly, in practical applications, position coordinates of the reference positioning patch Or may alternatively be used as a reference to calculate a position correspondence of a puncture needle t relative to the reference positioning patch Or, and then calculate a position correspondence of the reference positioning patch Or and the reference positioning patch Oi, so as to locate the intraoperative puncture needle.

According to the foregoing method, based on image data of a patient before puncture, quick segmentation is performed on a key anatomical structure, a lesion area, and a spatial positioning patch of a patient by using a deep learning technology, to further reconstruct a visual graphical interface. Based on information of the spatial positioning patch, an image coordinate system of the patient before puncture is further aligned with an actual physical coordinate system of the patient by using a spatial registration technology, and spatial posture information of the puncture needle relative to the patient is mapped to an image space in real time, so as to provide a doctor with visual and intuitive feedback of a patient's subcutaneous surgery, and a planned surgical path is provided for the doctor for further operation guide.

In practical applications, puncture may generally be divided into diagnostic puncture and therapeutic puncture. Common punctures include a thoracic puncture, an abdominal puncture, a lumbar puncture, an epidural puncture, a bone marrow puncture, a lung puncture, a joint cavity puncture, a vaginal posterior fornix puncture, a lymph node puncture, a body surface lump puncture, and the like. A solution provided in the embodiment of this specification is applicable to all puncture scenarios. Next, implementation of the technical solution provided in the embodiment of this specification in different puncture scenarios is described separately in the following implementation manners.

Implementation Manner 1

The lung puncture is used as an example to describe the technical solution provided in the embodiment of this specification.

In a pulmonary nodule puncture, target image data may further include key organ image data and lesion area image data of a detection target in addition to image data of a positioning patch. The lesion area image data may include pulmonary nodule image data; and the key organ image data may include body surface image data, skeleton image data, bronchus image data, lung lobe image data, and pulmonary blood vessel image data.

Optionally, the segmenting the image data to be identified by using a trained image segmentation model to obtain segmented target image data may specifically include:

inputting the image data to be identified into the trained image segmentation model, to obtain the key organ image data and lesion area image data of the detection target in the image data to be identified, and the image data of the positioning patches with the different features.

The segmentation may include: patient whole body segmentation, lung segmentation, pulmonary nodule detection, and classification and positioning of the positioning patches. Segmentation of key organs may be discussed separately in the following ways.

Body surface segmentation may be implemented by using a traditional threshold method, a watershed method, or a deep learning method to extract body surface image data of a patient.

Bone segmentation may be used to extract image skeletons based on a U-Net model, and the image skeletons may be further divided into six categories: ribs, vertebrae, scapulae, clavicle, thoracic vertebrae and pelvis, of which ribs may be further divided into 24 subcategories. A U-Net network model may be composed of an encoder (downsampler) and a decoder (upsampler). The encoder may be a trained MobileNet V2 model, and the decoder may use an upsampling module.

Bronchial segmentation is implemented in the follow manner: cutting a lung image into small-block images to perform an initial segmentation based on a ResUNet network; then connecting, by using a region growing algorithm, all the small-block images obtained through the initial segmentation, to form a complete bronchial segmentation result; and finally dividing a bronchus into 18 segments and 42 sub-segments in combination with a bronchial topology.

Lung lobe segmentation is implemented in the follow manner: cutting a lung image into small-block images to perform lung lobe extraction based on a ResUNet network, where all small-block images use a bottleneck structure; keeping a size of output to be the same as that of input, and introducing a Long Short-Term Memory (LSTM for short) module according to input data and a size of an output label to smooth an interlobar fissure; then connecting all the small-block images by using the region growing algorithm, to form three complete lung fissures; and finally segmenting a whole lung into five lobes based on a lung segmentation result and a lung fissure segmentation result, and segmenting the lung into 18 segments in combination with a watershed characteristic and 18 segments of a bronchus. Length, width, and height of DICOM data input to a network after cropping represent sizes, and output of a segmentation result represents an initial lung lobe segmentation result, which needs to be post-processed by introducing the LSTM module.

Pulmonary nodule detection is implemented by detecting a network algorithm by using a fully convolutional one-stage (FCOS) detection target, and further extracting a nodule target area by using a ResUNet network. FCOS may be a one-stage, fully convolutional object detection algorithm that predicts an object in a per-pixel manner, similar to semantic segmentation.

Pulmonary blood vessel segmentation may be implemented by using first-level segmentation classification combined with a second-level deep fix vessel solution. The first-level segmentation classification may use a UNet-like network structure combined with a patch-based method. A connectivity check module is added following a first-level network to check a result of blood vessel classification. If a connectivity check result is opposite to a blood flow trend, second-level deep vessel fix is started; otherwise, the result of the first-level network is retained. This method may effectively resolve a problem of misclassification of an artery and a vein in a first-level model by using a blood vessel connectivity feature.

Positioning patch extraction may be implemented based on a deep learning model. The deep learning model learns features of different the positioning patches. After training is completed, a trained deep learning model is used to identify a feature of a positioning patch in an image data to be identified, so as to detect and classify the positioning patch.

Specifically, features of the positioning patches may include: a shape feature, a size feature, a signal strength feature, and the like. During training, the deep learning model may be trained by using a corresponding feature according to an actual application scenario and identification requirement, which is not specifically limited in the embodiment of this specification.

The deep learning model provided in the embodiment of this specification may be used during image segmentation to not only obtain key organ image data through segmentation, but also identify lesion area data, such as pulmonary nodule image data, and identify image data of a positioning patch with different features. The training may be implemented based on the following process:

obtaining a training sample set of image data of a known image type, where the image type at least comprises an organ type, a lesion type, and a positioning patch type;

for each training sample in the training sample set, inputting a training sample into an initial deep learning model, and outputting an identification result; and adjusting, according to a difference between the identification result and the known image type, a model parameter of the initial deep learning model to obtain the trained image segmentation model.

Bottom-up unsupervised learning may be used as follows: Image data with calibration (calibration image type) is used to train parameters of each layer layer by layer, and parameters of the first layer are learned first during training. Due to limitation of model capability and a sparsity constraint, an obtained model can learn a structure of data itself, so as to obtain a feature that is more expressive than input. After the $(n-1)^{th}$ layer is obtain through learning, output of the $(n-1)^{th}$ layer is used as input of the nth layer for training the nth layer, and thus parameters of each layer are obtained separately. Top-down supervised learning may alternatively be used for training as follows: Parameters of an entire multi-layer model are further fine-tuned based on the parameters of each layer obtained in the first step, which is similar to an initial value random initialization process of a neural network.

In an embodiment, an image segmentation model may be a fully connected deep neural network (DNN) model. The fully connected deep neural network model may include an input layer and a plurality of fully connected layers. The input layer may be connected to output of the encoder, and the input layer may also be connected to the fully-connected layers. The input layer is used to receive a coding vector output by the encoder. The fully-connected layer is used to perform feature extraction on the coding vector, to obtain an image type vector of a target to be detected. The fully-connected deep neural network model may further include an output layer, and the output layer may be connected to the fully-connected layer. The output layer may be used to generate an image segmentation result based on the image type vector output by the fully-connected layer. The image type vector output by the fully-connected layer is an output vector of a fully connected layer adjacent to the output layer.

In the embodiment of this specification, a training target of an autoencoder is to segment the image data to be identified, and the deep neural network model may be used for a classification scenario. Therefore, when the image data to be identified of the target to be detected is input into the deep neural network, an output vector of the deep neural network model may be an image vector of each segmented image. Certainly, in the embodiment of this specification, the deep neural network model carried in a guide information generating device may be either a fully connected deep neural network model or a non-fully connected deep neural network model. The fully connected deep neural network model refers to that any neuron in the ith layer in the model is connected to each neuron in the $(i+1)^{th}$ layer, and the non-fully connected deep neural network model refers to that any neuron in the ith layer in the model may be connected to some neurons in the $(i+1)^{th}$ layer. Compared with the non-fully connected deep neural network model, the fully connected deep neural network model may extract more image feature information, but also needs a large amount of calculation, easily affecting computational efficiency. Therefore, the deep neural network model carried in the guide information generating device may be determined according to an actual requirement.

In the embodiment of this specification, a fully connected layer (FC) may function as a "classifier". A quantity of fully connected layers in a deep neural network model is proportional to a nonlinear expression ability of the model. Therefore, when the deep neural network model includes a plurality of fully connected layers, accuracy of each segmented image feature generated based on the deep neural network model may be improved. In practical applications, a feature vector of the segmented image may be either an output vector of a fully connected layer adjacent to the output layer, or an output vector of a fully connected layer separated from the output layer by N network layers, which is not specifically limited herein.

Implementation Manner 2

A liver puncture is used as an example to describe the technical solution provided in the embodiment of this specification.

Target image data may include key organ image data and lesion area image data of a detection target, and image data of the positioning patches. The lesion area image data may include a space-occupying lesion or a tumor area. The key organ image data may include gallbladder image data, bile duct image data, and hepatic artery and vein image data. Image data to be identified may be processed based on a deep learning model to obtain the gallbladder image data, the bile duct image data, and the hepatic artery and vein image data that need to be avoided during puncture. Space-occupying lesion or tumor region image data as well as the image data of the positioning patches may also be identified. Compared with the foregoing Implementation manner 1, a difference of the specific implementation process only lies in an identification object. Segmentation of each key organ or lesion area may be performed by selecting an appropriate network structure in a deep learning network. Other implementations are the same as those in Implementation manner 1, and details are not repeated herein.

Implementation Manner 3

An intracranial puncture is used as an example to describe the technical solution provided in the embodiment of this specification.

Target image data may include key organ image data and lesion area image data of a detection target, and image data of the positioning patches. The lesion area image data may include hematoma or lesion area image data; and the key organ image data may include blood vessel image data, neural image data, and the like. Image data to be identified may be processed based on a deep learning model to obtain the blood vessel image data, neural image data, and the like that need to be avoided during puncture. Space-occupying lesion or tumor region image data as well as the image data of the positioning patches may also be identified. Compared with the foregoing Implementation manner 1, a difference of the specific implementation process only lies in an identification object. Segmentation of each key organ or lesion area may be performed by selecting an appropriate network structure in a deep learning network. Other implementations are the same as those in Implementation manner 1, and details are not repeated herein.

It should be noted that the foregoing Implementation manner 1 to Implementation manner 3 respectively provide three puncturing implementations, but in a practical application scenario, an application scope is not limited to the foregoing three implementation manners. All scenarios in which pathological puncture is required to determine whether a nodule is benign or malignant are applicable to the technical solution provided in the embodiment of this specification.

According to the method for generating guide information in the foregoing embodiment, at least the following technical effects may be achieved.

(1) Defects of poor surgical accuracy, large radiation damage, and invisible target area caused by a method of a plurality of times of CT pulmonary nodule puncture in traditional puncture may be overcome; and a plurality of positioning patches are used to track patient's posture, and the positioning patches are used as feature points, to implement efficient and rapid registration of DICOM image space and navigation positioning space.

(2) The positioning patches have different features. In an image detection process, an image segmentation model can be used to implement automatic distinction, so as to implement one-to-one matching with positioning information from an electromagnetic navigation system.

(3) Based on a deep learning technology, real-time needle insertion tracking and posture inspection during surgery is implemented in combination with a high-precision electromagnetic positioning system, and navigation planning is performed in conjunction with preoperative nodule and thoracic tissue segmentation, which is conducive to smooth progress of puncture surgery.

(4) Automatic detection and segmentation are implemented with faster speed by combining deep learning with a surgical navigation technology; automatic path planning is more intuitive for a doctor; and full surgical positioning of a patient and a puncture needle is implemented, which may greatly shorten an operation time.

Based on the same concept, an embodiment of this specification also provide a system for implementing the method in the foregoing embodiment.

Exemplary System

Next, a system for generating guide information according to an embodiment of this specification is specifically described below.

The system may include:

a puncture guiding device and positioning patches.

The puncture guiding device is communicatively connected to an image capturing device for receiving image data to be identified, captured by the image capturing device, of a detection target.

The positioning patches are communicatively connected to the puncture guiding device, the positioning patches is provided with a sensor, and the sensor transmits position information of the positioning patches to the puncture guiding device.

The puncture guiding device segments the image data to be identified by using a trained image segmentation model to obtain segmented target image data, and the target image data at least includes image data of positioning patches arranged on a body surface of the detection target.

The image data of the positioning patches are determined as feature points, and a mapping relationship between a preoperative spatial three-dimensional image coordinate system and an intraoperative spatial positioning coordinate system is established.

Guide information is generated based on the mapping relationship, and the guide information is used to guide a puncture needle to perform puncturing on the detection target.

The system for generating guide information may be divided into a software part and a hardware part, which will be described separately with reference to accompanying drawings.

Figure 3:
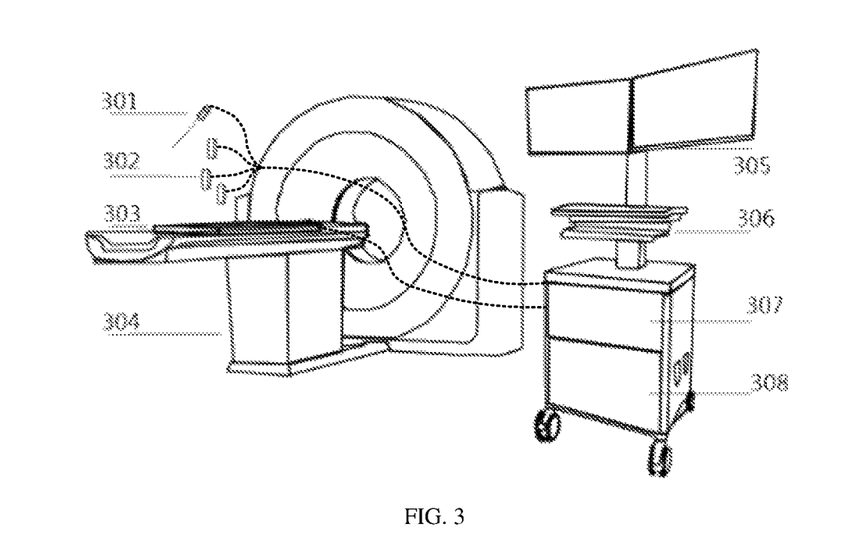
FIG. 3 is a schematic diagram of a hardware apparatus in a system for generating guide information according to an embodiment of this specification.

The hardware part may be described with reference to FIG. 3. FIG. 3 is a schematic diagram of a hardware apparatus in a system for generating guide information according to an embodiment of this specification. As shown in FIG. 3, the hardware apparatus may include a puncture needle 301, the positioning patches 302 (number≥3), a magnetic field generator 303, a CT machine 304, a visual graphic interface 305, a keyboard and mouse peripheral 306, and a navigation tracker control unit 307, a server and power supply 308. A 6 Degree of Freedom (6DOF) electromagnetic sensor is disposed in all of the puncture needle 301 and each positioning patch 302, and the navigation tracker control unit 307 may locate a spatial posture of the detection target. The magnetic field generator 303 is placed flat on the CT machine 304 during a puncture operation, and communicates with the navigation tracker control unit 307 through a connecting line. Uninterruptible power supply in the server and power supply 308 may ensure a normal operation of the whole system after a sudden power failure, and an operating system and a whole set of puncture software are deployed on the server. It should be noted that, although the positioning patches in FIG. 3 seems to have a same shape, it does not mean that features of the positioning patches are the same. In practical applications, shapes of the positioning patches may be different. Even if having a same shape, the positioning patches may be different in other features, for example, may be different in transmit signal strength.

It should be noted that, as an example, to clearly show a connection and communication relationship between the structures in FIG. 3, the puncture needle 301, the positioning patch 302, and the magnetic field generator 303 are all connected to the navigation tracker control unit 307 through a connecting wire. However, in practical applications, wireless connection may alternatively be used. For example, a signal transmitter is installed on the puncture needle 301 and the positioning patch 302 to implement communication with the navigation tracker control unit by means of signal transmission.

Figure 4:
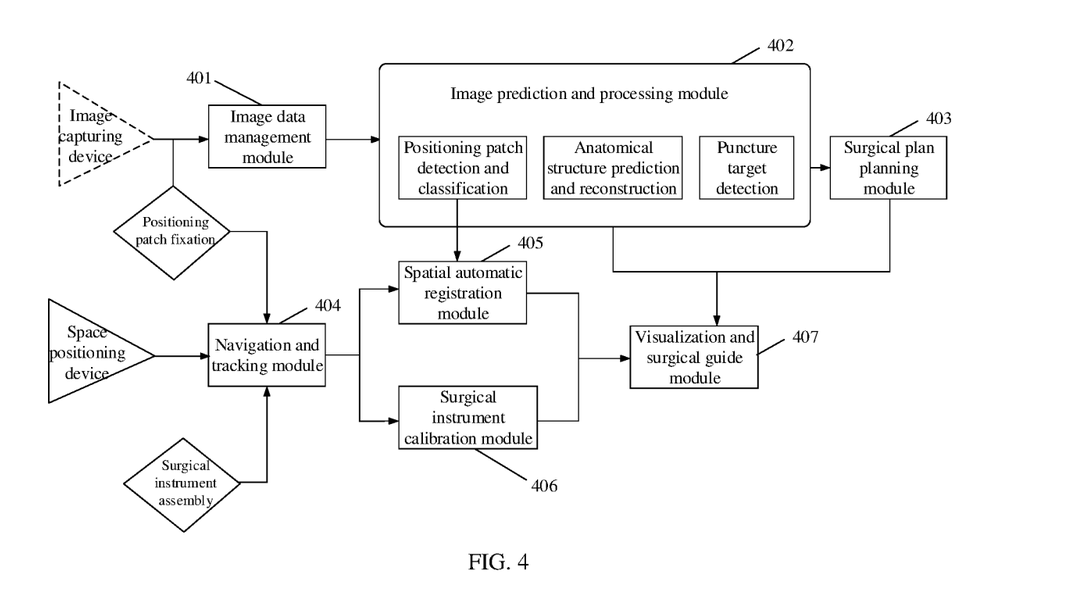
FIG. 4 is a schematic diagram of a software structure in a system for generating guide information according to an embodiment of this specification.

The hardware part may be described with reference to FIG. 4. FIG. 4 is a schematic diagram of a software structure in a system for generating guide information according to an embodiment of this specification. As shown in FIG. 4, the software part may include: an image data management module 401, an image prediction and processing module 402, a surgical plan planning module 403, a navigation and tracking module 404, a spatial automatic registration module 405, a surgical instrument calibration module 406, and a visualization and surgical guide module 407.

The image data management module 401 may be a Docking Station (DS) module, which may include an information pulling component, a preprocessing component, and a data sending component. The information pulling component may receive DICOM image data pushed by a hospital information system. The preprocessing component may filter and screen the image data obtained by the pulling component according to a rule deployed in a DS service configuration file. The data sending component may receive a sequence obtained based on screening of the preprocessing component and send the data to an InferX data center by using an HTTP POST request.

The image prediction and processing module 402 may be described with reference to FIG. 5.

Figure 5:
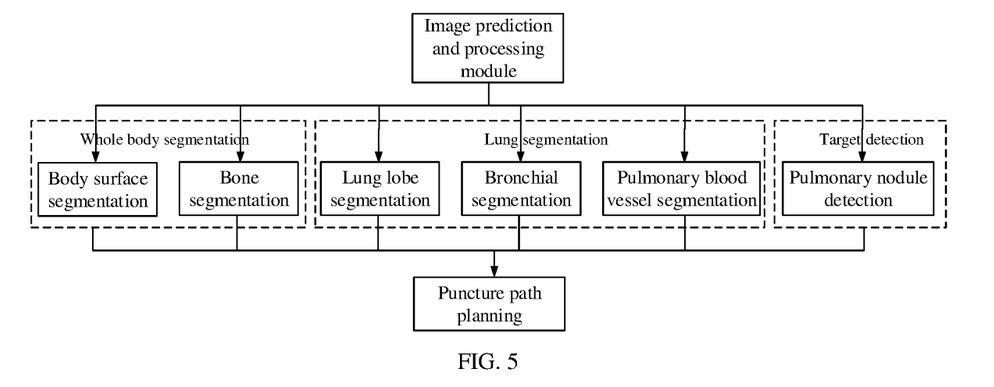
FIG. 5 is a schematic diagram of an image prediction and processing module according to an embodiment of this specification.

FIG. 5 is a schematic diagram of an image prediction and processing module according to an embodiment of this specification. As shown in FIG. 5, a pulmonary nodule puncture is used as an example. The image prediction and processing module 402 may process a patient DICOM image output by the image data management module based on a prediction task deployed in the DS. The prediction task consists of four parts: patient whole body segmentation, lung segmentation, pulmonary nodule detection, and classification and positioning of the positioning patches. The whole body segmentation may include body surface segmentation and bone segmentation. The lung segmentation may include lung lobe segmentation, bronchial segmentation, and pulmonary blood vessel segmentation. Target detection may be pulmonary nodule detection. The whole body segmentation, the lung segmentation and pulmonary nodule detection are inputs to a puncture path planning module.

The surgical plan planning module 403 may automatically design a puncture path for a pulmonary nodule detected by the image prediction and processing module according to a clinical lung puncture rule. A puncture path for each nodule may include a needle insertion point, a needle insertion direction, and a needle insertion distance. Planning of a puncture path relies on a segmentation result of various organs in the image prediction and processing module, which is to ensure that the puncture path avoids ribs and important organs. The puncturing rule has been described in the foregoing embodiments, and will not be repeated herein.

The navigation and tracking module 404 may be configured to track the positioning patches and position information of a puncture needle during a puncture operation. The preoperative image data in the embodiment of this specification may include image information of the patient, the positioning patches, a magnetic field generator, and the like. At least three positioning patches may be used. Before the puncture operation, specifically, before obtaining of puncture image data, the magnetic field generator is placed flat on a CT machine, and the patient lies on the magnetic field generator (in the front, side or prone position) according to a doctor's requirement. The positioning patches are fixed to the body surface of the patient to avoid any three patches being linearly distributed and to avoid patch displacement during a puncture procedure. Displacement refers to position movement of a patch relative to a local body surface of the patient.

The positioning patches are used to track a posture of the patient during surgery, and the positioning patches of different shapes may be used to implement identification and positioning of each positioning patch in the image data. The positioning patches with different shapes are in a one-to-one correspondence with an interface of a navigation tracker control unit. The puncture needle is provided with a sensor adapter buckle at a position of the needle end for connecting a positioning sensor.

The spatial automatic registration module 405 may implement registration of a positioning space of a navigation tracker.

The surgical instrument calibration module 406 may be used to calibrate a surgical instrument, such as the puncture needle.

The visualization and surgery guide module 407 may include an image display area and an information list area. The information list area may be used to display relevant information of a pulmonary nodule lesion area and all anatomical structures. The image display area may be used to display images of a plurality of follow-up visits, and has all image manipulation functions of a picture archiving and communication system (PACS), including but not limited to: window width and level adjustment, measurement, position probe, multi-image linkage function. A logic of multi-image linkage comes from a mapping relationship between two images output through image registration.

At the beginning of an operation, both a probe needle and a positioning patch need to be placed within a magnetic field range of the magnetic field generator. An intraoperative navigation and tracking module constructs a position and a posture of the probe needle in a CT image space based on a relative position and angle transformation of the probe needle and the positioning patch, and calculates a distance of the probe needle from a lesion, pleura and the like along a current angle. All these are displayed in a three-dimensional tissue interface through a display. Therefore, the system for generating guide information may further include a display device, and the display device may be configured to receive guide information sent by an image capturing device, and display the guide information on a display screen of the display device. Besides, the system for generating guide information may further include the image capturing device for capturing image data of a patient.

Corresponding to the foregoing method embodiment, the exemplary system is also applicable to an application scenario such as a lung puncture or an abdominal puncture. According to the foregoing system for generating guide information, in combination with a deep learning technology and high-precision positioning, efficient and rapid registration of DICOM image space and navigation and positioning space may be implemented. The generated guide information may provide intuitive feedback on a relative position between an anatomical structure of the detection target and the puncture needle as well as between the puncture needle and a planned path, so that a doctor can visualize an anatomical structure of the patient's chest or abdomen and formulate a reasonable surgical plan. In addition, during a puncture operation, intuitive feedback on a relative position between an anatomical structure of a patient and the puncture needle as well as between the puncture needle and the planned path is obtained. This greatly shortens an operation time, and improves puncture efficiency and accuracy.

Exemplary Apparatuses

Figure 6:
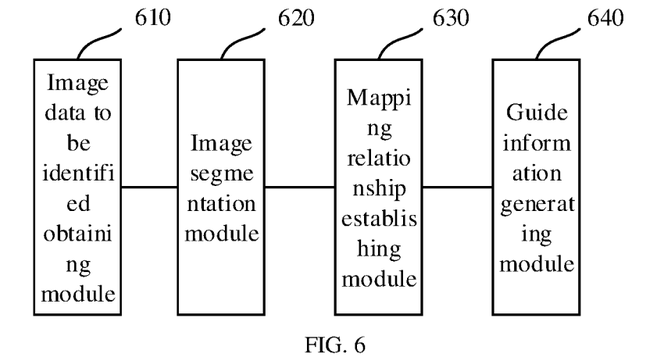
FIG. 6 is a schematic structural diagram of an apparatus for generating guide information according to an embodiment of this specification.

Based on the same concept, an embodiment of this specification further provides an apparatus corresponding to the method in the foregoing embodiment. FIG. 6 is a schematic structural diagram of an apparatus for generating guide information according to an embodiment of this specification. As shown in FIG. 6, the apparatus may include:

- an image data to be identified obtaining module 610, configured to obtain image data to be identified of a detection target;
- an image segmentation module 620, configured to segment the image data to be identified by using a trained image segmentation model to obtain segmented target image data, where the target image data at least includes image data of positioning patches arranged on a body surface of the detection target;
- a mapping relationship establishing module 630, configured to determine the image data of the positioning patches as feature points, and establish a mapping relationship between a preoperative spatial three-dimensional image coordinate system and an intraoperative spatial positioning coordinate system; and
- a guide information generating module 640, configured to generate guide information based on the mapping relationship, where the guide information is used to guide a puncture needle to perform puncturing on the detection target.

Based on the apparatus illustrated in FIG. 6, an embodiment of this specification further provides some specific implementations of the apparatus, which are described below.

Optionally, the positioning patches may have different features.

Optionally, the mapping relationship establishing module 630 may specifically include:

- a positioning patch image data obtaining unit, configured to obtain preoperative image data of the positioning patches and intraoperative spatial positioning data of the positioning patches;
- a spatial position information obtaining unit, configured to obtain first position information of each positioning patch in the preoperative image data;
- an actual position information obtaining unit, configured to obtain second position information of each positioning patch in the intraoperative spatial positioning data; and
- a mapping relationship establishing unit, configured to establish the mapping relationship between the preoperative spatial three-dimensional image coordinate system and the intraoperative spatial positioning coordinate system based on the first position information and the second position information.

Optionally, the guide information generating module 640 may specifically include:

- a puncture path determining unit, configured to determine, based on the mapping relationship and according to a preset puncture rule, a puncture path for performing puncturing on the detection target, where the puncture path at least includes a needle insertion point, a needle insertion direction, and a needle insertion distance.

Optionally, the guide information generating module 640 may specifically include:

- a third position information determining unit, configured to obtain third position information of the puncture needle in the preoperative image data;

a relative position information determining unit, configured to determine, based on the first position information and the third position information, relative position information of the puncture needle and the positioning patches; and a guide information generation unit, configured to generate the guide information based on the relative position information and the mapping relationship.

Optionally, the guide information generation unit may specifically include:
 a reference positioning patch determining subunit, configured to determine any one of the positioning patches in the preoperative image data as a reference positioning patch;
 a position coordinate obtaining subunit, configured to obtain position coordinates of the reference positioning patch;
 a first position correspondence calculation subunit, configured to calculate, by using the position coordinates of the reference positioning patch as a reference, a first position correspondence between another positioning patch in the preoperative image data and the reference positioning patch;
 a second position correspondence calculation subunit, configured to calculate a second position correspondence between the reference positioning patch in the preoperative image data and the reference positioning patch in the intraoperative spatial positioning data;
 a puncture needle position information calculation subunit, configured to calculate, based on the first position correspondence and the second position correspondence, position information of an intraoperative puncture needle in the intraoperative spatial positioning data; and a guide information generation subunit, configured to generate the guide information based on the mapping relationship and the position information of the intraoperative puncture needle in the intraoperative spatial positioning data.

Optionally, the target image data may further include key organ image data and lesion area image data of the detection target. The lesion area image data may include pulmonary nodule image data; and the key organ image data may include: body surface image data, skeleton image data, bronchus image data, lung lobe image data, and pulmonary blood vessel image data.

The image segmentation module 620 may specifically include:
 an image segmentation unit, configured to input the image data to be identified into the trained image segmentation model, to obtain the key organ image data and lesion area image data of the detection target in the image data to be identified, and the image data of the positioning patch with the different features.

Optionally, the skeleton image data may be extracted based on a UNet network structure.

Optionally, the image segmentation unit may be specifically configured to:
 perform, by using a ResUNet network, initial segmentation on the image data to be identified to obtain a first segmentation result, where the first segmentation result includes a plurality of pieces of block image data; and
 connect, by using a region growing algorithm, the plurality of pieces of block image data in the first segmentation result to obtain the bronchus image data.

Optionally, the image segmentation unit may be specifically configured to:
 process, by using a long short-term memory network, the first segmentation result; and
 connect, by using the region growing algorithm, processed segmentation results to obtained the lung lobe image data.

Optionally, the image segmentation unit may be specifically configured to:
 detect, by using an FCOS algorithm, pulmonary nodule information from the image data to be identified; and
 extract, by using the ResUNet network, the pulmonary nodule image data after the pulmonary nodule information is detected.

Optionally, the positioning patches may be in different shapes. The image segmentation unit may be specifically configured to:
 identify information of the positioning patches with different shapes from the image data to be identified; and
 extract the image data of the positioning patches after the information of the positioning patches in the image data to be identified is identified.

Optionally, the positioning patches may have different intensity signals. The image segmentation unit may be specifically configured to:
 identify information of the positioning patches corresponding to different intensity signals from the image data to be identified; and
 extract the image data of the positioning patches after the information of the positioning patches in the image data to be identified is identified.

Optionally, the image data to be identified obtaining module 610 may specifically include:
 an image data obtaining unit, configured to obtain DICOM image data, pushed by a hospital information system, of the detection target.

Optionally, the apparatus may further include:
 a training sample set obtaining module, configured to obtain a training sample set of image data of a known image type, where the image type at least includes an organ type, a lesion type, and a positioning patch type;
 a training module, configured to: for each training sample in the training sample set, input a training sample into an initial deep learning model, and output an identification result; and
 a parameter adjustment module, configured to adjust, according to a difference between the identification result and the known image type, a model parameter of the initial deep learning model to obtain the trained image segmentation model.

Optionally, the image data to be identified may be image data obtained after screening according to a preset preprocessing rule.

Optionally, the positioning patches are fixed on a body surface of the detection target;
 and a quantity of the positioning patches is greater than or equal to three.

Optionally, the skeleton image data may include image data of at least one of a rib, a vertebra, a scapula, a clavicle, a thoracic vertebra, and a pelvis.

Optionally, the target image data may further include key organ image data and lesion area image data of the detection target, where the lesion area image data may include a space-occupying lesion or a tumor area; and the key organ image data may include gallbladder image data, bile duct image data, and hepatic artery and vein image data.

Based on the same concept, an embodiment of this specification further provides a device corresponding to the method in the foregoing embodiment.

Exemplary Device

Figure 7:
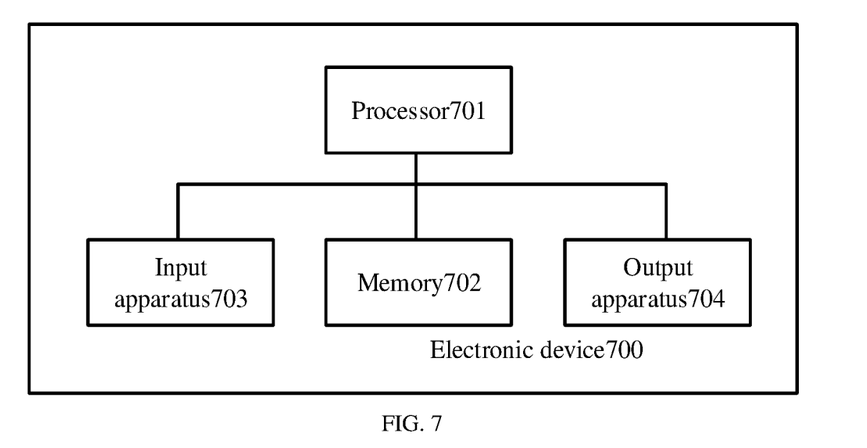
FIG. 7 is a schematic structural diagram of an electronic device according to an embodiment of this specification.

FIG. 7 is a schematic structural diagram of an electronic device according to an embodiment of this specification. As shown in FIG. 7, an electronic device 700 includes one or more processors 701 and a memory 702.

The processor 701 may be a Central Processing Unit (CPU) or a processing unit in another form that has a data handling capacity and/or instruction execution capacity, and may control another component in the electronic device 700 to perform a desired function.

The memory 702 may include one or more computer program products. The computer program product may include computer-readable storage mediums in various forms, for example, a volatile memory and/or a non-transitory memory. The volatile memory may include, for example, a random access memory (RAM) and/or a high-speed buffer memory (cache). The non-transitory memory may include, for example, a read-only memory (ROM), a hard disk, or a flash memory. The computer-readable storage medium may store one or more computer program instructions. The processor 701 may run the program instructions to implement the method for generating guide information according to the foregoing embodiments of the present application or another desired function.

In an example, the electronic device 700 may further include an input apparatus 703 and an output apparatus 704. These components may be interconnected to each other by using a bus system and/or a connecting mechanism in another form (not shown in the figure).

For example, the input apparatus 703 may be the instrument for detecting a sequence of non-enhanced CT images.

The output apparatus 704 may output various information to an external device, such as first coronary artery calcification data corresponding to a coronary artery segmented image. The output apparatus 704 may include, for example, a display, a printer, a communication network, and a remote output device connected thereto.

Certainly, for simplicity, FIG. 7 only shows some of components in the electronic device 700 that are related to the present application, and does not show components such as a bus, and an input/output interface. In addition, according to a specific application situation, the electronic device 700 may further include another proper component.

Corresponding to the foregoing method embodiment, the exemplary apparatus, the exemplary device, the exemplary computer program product, and the computer-readable storage medium are also applicable to an application scenario such as a lung puncture or an abdominal puncture. For example, scenarios such as a lung puncture, an abdominal puncture, and an intracranial puncture may be implemented by using the solution in the embodiment of this specification, which are not specifically limited in the embodiment of this specification.

Exemplary Computer Program Product and Computer-Readable Storage Medium

In addition to the foregoing methods and devices, an embodiment of the present application may alternatively be a computer program product, where the computer program product includes a computer program instruction. When the computer program instruction is run by a processor, the processor performs the steps of the method for generating guide information according to the embodiments of the present application described in section "Exemplary Method" of this specification.

The computer program product may use any combination of one or more programming languages to write a program code for performing operations in the embodiments of the present application. The programming languages include an object oriented programming language, such as Java, C++, and a conventional procedural programming language, such as the "C" language or a similar programming language. The program code may be entirely executed on a user's computing device, partially on a user's computing device, executed as an independent software package, partially executed on a user's computing device and partially executed on a remote computing device, or entirely executed on a remote computing device or a server.

In addition, an embodiment of this specification may further provide a computer-readable storage medium. The computer-readable storage medium stores computer program instructions. When the computer program instruction is run by a processor, the processor performs the steps of the method for generating guide information according to the embodiments of this specification described in section "Exemplary Method" of this specification.

The computer-readable storage medium may use any combination of one or more readable media. The readable medium may be a readable signal medium or readable storage medium. The readable storage medium may include, for example, but not limited to, an electronic, magnetic, optical, electromagnetic, infrared, or semiconductor system, apparatus, or means, or any combination thereof. More specific examples (a non-exhaustive list) of the readable storage medium include: an electrical connection having one or more wires, a portable disk, a hard disk, a random access memory (RAM), a read-only memory (ROM), an erasable programmable read-only memory (EPROM or a flash memory), an optical fiber, a portable compact disk read only memory (CD-ROM), an optical storage means, a magnetic storage means, or any suitable combination thereof.

The foregoing description has been given for the purposes of illustration and description. In addition, the description is not intended to limit the embodiments of the present application to the form disclosed herein. Although a quantity of exemplary aspects and embodiments have been discussed above, those skilled in the art will recognize some variations, modifications, changes, additions, and sub-combinations thereof.

What is claimed is:

1. A method for generating guide information, applied to a puncture guiding device connected to positioning patches and an image capturing device, comprising:

obtaining image data to be identified of a detection target;

segmenting the image data to be identified by using a trained image segmentation model to obtain segmented target image data, wherein the target image data at least comprises image data of positioning patches arranged on a body surface of the detection target, and the positioning patches have different sizes or intensity signals, and any three of the positioning patches are distributed in a non-linear manner;

identifying information of the positioning patches corresponding to different intensity signals from the image data to be identified;

extracting the image data of the positioning patches after the information of the positioning patches in the image data to be identified is identified;

determining the image data of the positioning patches as feature points, and establishing a mapping relationship between a preoperative spatial three-dimensional image coordinate system and an intraoperative spatial positioning coordinate system; and generating guide information based on the mapping relationship, wherein the guide information is used to guide a puncture needle to perform puncturing on the detection target.

2. The method according to claim 1, wherein the determining the image data of the positioning patches as feature points, and establishing a mapping relationship between a preoperative spatial three-dimensional image coordinate system and an intraoperative spatial positioning coordinate system comprises:

obtaining preoperative image data of the positioning patches and intraoperative spatial positioning data of the positioning patches;

obtaining first position information of each positioning patch in the preoperative image data;

obtaining second position information of each positioning patch in the intraoperative spatial positioning data; and establishing the mapping relationship between the preoperative spatial three-dimensional image coordinate system and the intraoperative spatial positioning coordinate system based on the first position information and the second position information.

3. The method according to claim 2, wherein the generating guide information based on the mapping relationship comprises:

obtaining third position information of the puncture needle in the preoperative image data;

determining, based on the first position information and the third position information, relative position information of the puncture needle and the positioning patches; and generating the guide information based on the relative position information and the mapping relationship.

4. The method according to claim 3, wherein the generating the guide information based on the relative position information and the mapping relationship comprises:

determining any one of the positioning patches in the preoperative image data as a reference positioning patch;

obtaining position coordinates of the reference positioning patch;

calculating, by using the position coordinates of the reference positioning patch as a reference, a first position correspondence between the reference positioning patch and another positioning patch in the preoperative image data;

calculating a second position correspondence between the reference positioning patch in the preoperative image data and the reference positioning patch in the intraoperative spatial positioning data;

calculating, based on the first position correspondence and the second position correspondence, position information of an intraoperative puncture needle in the intraoperative spatial positioning data; and generating the guide information based on the mapping relationship and the position information of the intraoperative puncture needle in the intraoperative spatial positioning data.

5. The method according to claim 1, wherein the generating guide information based on the mapping relationship comprises:

determining, based on the mapping relationship and according to a preset puncture rule, a puncture path for performing puncturing on the detection target, wherein the puncture path at least comprises a needle insertion point, a needle insertion direction, and a needle insertion distance.

6. The method according to claim 1, wherein the target image data further comprises key organ image data and lesion area image data of the detection target, wherein the lesion area image data comprises: pulmonary nodule image data; and the key organ image data comprises: body surface image data, skeleton image data, bronchus image data, lung lobe image data, and pulmonary blood vessel image data; and the segmenting the image data to be identified by using a trained image segmentation model to obtain segmented target image data comprises:

inputting the image data to be identified into the trained image segmentation model, to obtain the key organ image data and lesion area image data of the detection target in the image data to be identified, and the image data of the positioning patches with the different features.

7. The method according to claim 6, wherein the skeleton image data is extracted based on a UNet network structure;

the extraction of the bronchus image data specifically comprises:

performing, by using a ResUNet network, initial segmentation on the image data to be identified to obtain a first segmentation result, wherein the first segmentation result comprises a plurality of pieces of block image data; and connecting, by using a region growing algorithm, the plurality of pieces of block image data in the first segmentation result to obtain the bronchus image data;

the extraction of the lung lobe image data specifically comprises:

processing, by using a long short-term memory network, the first segmentation result; and connecting, by using the region growing algorithm, processed segmentation results to obtain the lung lobe image data;

the extraction of the pulmonary nodule image data specifically comprises:

detecting, by using an FCOS algorithm, pulmonary nodule information from the image data to be identified; and extracting, by using the ResUNet network, the pulmonary nodule image data after the pulmonary nodule information is detected.

8. The method according to claim 1, wherein the obtaining image data to be identified of a detection target comprises:

obtaining DICOM image data, pushed by a hospital information system, of the detection target.

9. The method according to claim 1, wherein before the segmenting the image data to be identified by using a trained image segmentation model to obtain segmented target image data, the method further comprises:

obtaining a training sample set of image data of a known image type, wherein the image type at least comprises an organ type, a lesion type, and a positioning patch type;

for each training sample in the training sample set, inputting a training sample into an initial deep learning model, and outputting an identification result; and adjusting, according to a difference between the identification result and the known image type, a model parameter of the initial deep learning model to obtain the trained image segmentation model.

10. A non-transitory computer-readable storage medium, wherein the non-transitory computer-readable storage medium stores computer program instructions, and when the computer program instructions are run by a processor, the processor is configured to implement the method according to claim 1.

11. A system for generating guide information, comprising:
a puncture guiding device and positioning patches, wherein
the puncture guiding device is communicatively connected to an image capturing device; and
the positioning patches are communicatively connected to the puncture guiding device, and the puncture guiding device comprises a processor and a memory, wherein the memory stores computer program instructions, and when the computer program instructions are run by the processor, the processor is configured to implement the following steps:
receiving image data to be identified of a detection target, captured by the image capturing device;
segmenting the image data to be identified by using a trained image segmentation model to obtain segmented target image data, wherein the target image data at least comprises image data of positioning patches arranged on a body surface of the detection target, and the positioning patches have different sizes or intensity signals, and any three of the positioning patches are distributed in a non-linear manner;
identifying information of the positioning patches corresponding to different intensity signals from the image data to be identified; and
extracting the image data of the positioning patches after the information of the positioning patches in the image data to be identified is identified;
determining the image data of the positioning patches as feature points, and establishing a mapping relationship between a preoperative spatial three-dimensional image coordinate system and an intraoperative spatial positioning coordinate system; and
generating guide information based on the mapping relationship, wherein the guide information is used to guide a puncture needle to perform puncturing on the detection target.

12. The system according to claim 11, wherein the determining the image data of the positioning patches as feature points, and establishing a mapping relationship between a preoperative spatial three-dimensional image coordinate system and an intraoperative spatial positioning coordinate system comprises:
obtaining preoperative image data of the positioning patches and intraoperative spatial positioning data of the positioning patches;
obtaining first position information of each positioning patch in the preoperative image data;
obtaining second position information of each positioning patch in the intraoperative spatial positioning data; and
establishing the mapping relationship between the preoperative spatial three-dimensional image coordinate system and the intraoperative spatial positioning coordinate system based on the first position information and the second position information.

13. The system according to claim 12, wherein the generating guide information based on the mapping relationship comprises:
obtaining third position information of the puncture needle in the preoperative image data;
determining, based on the first position information and the third position information, relative position information of the puncture needle and the positioning patches; and
generating the guide information based on the relative position information and the mapping relationship.

14. The system according to claim 13, wherein the generating the guide information based on the relative position information and the mapping relationship comprises:
determining any one of the positioning patches in the preoperative image data as a reference positioning patch;
obtaining position coordinates of the reference positioning patch;
calculating, by using the position coordinates of the reference positioning patch as a reference, a first position correspondence between the reference positioning patch and another positioning patch in the preoperative image data;
calculating a second position correspondence between the reference positioning patch in the preoperative image data and the reference positioning patch in the intraoperative spatial positioning data;
calculating, based on the first position correspondence and the second position correspondence, position information of an intraoperative puncture needle in the intraoperative spatial positioning data; and
generating the guide information based on the mapping relationship and the position information of the intraoperative puncture needle in the intraoperative spatial positioning data.

15. The system according to claim 11, wherein the generating guide information based on the mapping relationship comprises:
determining, based on the mapping relationship and according to a preset puncture rule, a puncture path for performing puncturing on the detection target, wherein the puncture path at least comprises a needle insertion point, a needle insertion direction, and a needle insertion distance.

16. The system according to claim 11, further comprising:
a display device, configured to receive guide information sent by the image capturing device, and display the guide information on a display screen of the display device.

* * * * *